(12) United States Patent
Bicakci et al.

(10) Patent No.: US 6,500,145 B1
(45) Date of Patent: Dec. 31, 2002

(54) RETROGRADE CARDIOPLEGIA CATHETER

(75) Inventors: Mehmet Bicakci, Santa Ana, CA (US); Sheryl W. Higgins, Silverado, CA (US)

(73) Assignee: California Medical Laboratories, Inc., Costa Mesa, CA (US)

( * ) Notice: Subject to any disclaimer, the term of this patent is extended or adjusted under 35 U.S.C. 154(b) by 0 days.

(21) Appl. No.: 09/499,796

(22) Filed: Feb. 8, 2000

(51) Int. Cl.⁷ ............................................. A61M 29/00
(52) U.S. Cl. ............................... 604/96.01; 604/97.01; 604/99.01; 604/98.01
(58) Field of Search ....................... 604/96.01, 97.01, 604/99.01, 99.02, 99.03, 97.03, 98.01, 99.04, 100.01, 100.03; 606/191, 192; 607/116

(56) References Cited

U.S. PATENT DOCUMENTS

| | | | |
|---|---|---|---|
| 4,323,071 A | * 4/1982 | Simpson et al. | 604/97.01 |
| 4,648,384 A | 3/1987 | Schmuckler | |
| 4,684,363 A | * 8/1987 | Ari et al. | 604/98.01 |
| 4,689,041 A | 8/1987 | Corday | |
| 4,714,460 A | 12/1987 | Calderon | |
| 4,753,637 A | 6/1988 | Horneffer | |
| 4,867,742 A | 9/1989 | Calderon | |
| 4,875,481 A | * 10/1989 | Higgins | 604/96.01 |
| 4,943,277 A | 7/1990 | Bolling | |
| 5,021,045 A | 6/1991 | Buckberg | |
| 5,033,998 A | 7/1991 | Corday | |
| 5,087,247 A | * 2/1992 | Horn et al. | 604/98.01 |
| 5,090,958 A | * 2/1992 | Sahota | 604/98.01 |
| 5,100,383 A | * 3/1992 | Lichtenstein | 604/98.01 |
| 5,197,952 A | 3/1993 | Marcadis | |
| 5,226,427 A | 7/1993 | Buckberg | |
| 5,275,597 A | * 1/1994 | Higgins et al. | 607/116 |
| 5,320,604 A | * 6/1994 | Walker et al. | 604/99.04 |
| 5,324,260 A | 6/1994 | O'Neill | |
| 5,383,890 A | * 1/1995 | Miraki et al. | 604/99.04 |
| 5,385,548 A | 1/1995 | Williams | |
| 5,395,331 A | 3/1995 | O'Neill | |
| 5,423,745 A | 6/1995 | Todd | |
| 5,454,788 A | * 10/1995 | Walker et al. | 604/99.04 |
| 5,486,192 A | * 1/1996 | Walinsky et al. | 604/98.01 |
| 5,506,698 A | 4/1996 | Booth | |
| 5,558,644 A | 9/1996 | Boyd | |
| 5,584,803 A | 12/1996 | Stevens | |
| 5,620,418 A | 4/1997 | O'Neill | |
| 5,653,690 A | 8/1997 | Booth | |
| 5,707,358 A | 1/1998 | Wright | |
| 5,738,652 A | 4/1998 | Boyd | |
| 5,779,685 A | 7/1998 | Thompson | |
| 5,807,326 A | 9/1998 | O'Neill | |
| 5,807,328 A | 9/1998 | Briscoe | |
| 5,833,658 A | * 11/1998 | Levy et al. | 604/97.01 |
| 5,913,842 A | 6/1999 | Boyd | |
| 5,980,503 A | 11/1999 | Chin | |
| 6,179,827 B1 | * 1/2001 | Davis et al. | 604/97.01 |

FOREIGN PATENT DOCUMENTS

| | | |
|---|---|---|
| EP | 0 841 073 A2 | 5/1998 |
| EP | 0 853 954 A2 | 7/1998 |
| EP | 0 567 976 B1 | 7/1999 |
| WO | WO 89/10155 | 11/1989 |

* cited by examiner

*Primary Examiner*—Teresa Walberg
*Assistant Examiner*—Fadi H. Dahbour
(74) *Attorney, Agent, or Firm*—Knobbe, Martens, Olson & Bear, LLP

(57) ABSTRACT

Disclosed is a catheter having an elongated cannula with an infusion lumen and a pressure-sensing lumen, and a portion of the cannula which tapers to form a distal end which is narrower than the more proximal portions of the cannula. The distal end of the cannula has a rounded tip and forms at least one infusion lumen opening and a pressure-sensing opening. A balloon is attached to and surrounds the cannula near the distal end while being in fluid communication with the infusion lumen through one or more inflation openings. The infusion lumen openings are smaller than the inflation openings so as to make the balloon self-inflating. Also disclosed is a method for using such a catheter to perform cardioplegia by the retrograde infusion of a cardioplegic fluid into the coronary sinus.

28 Claims, 4 Drawing Sheets

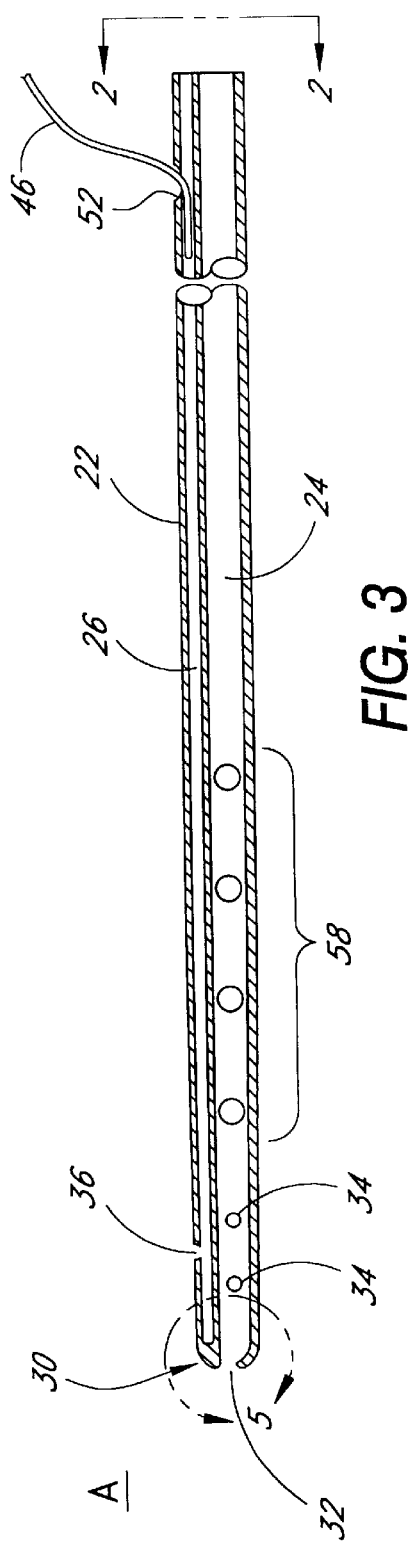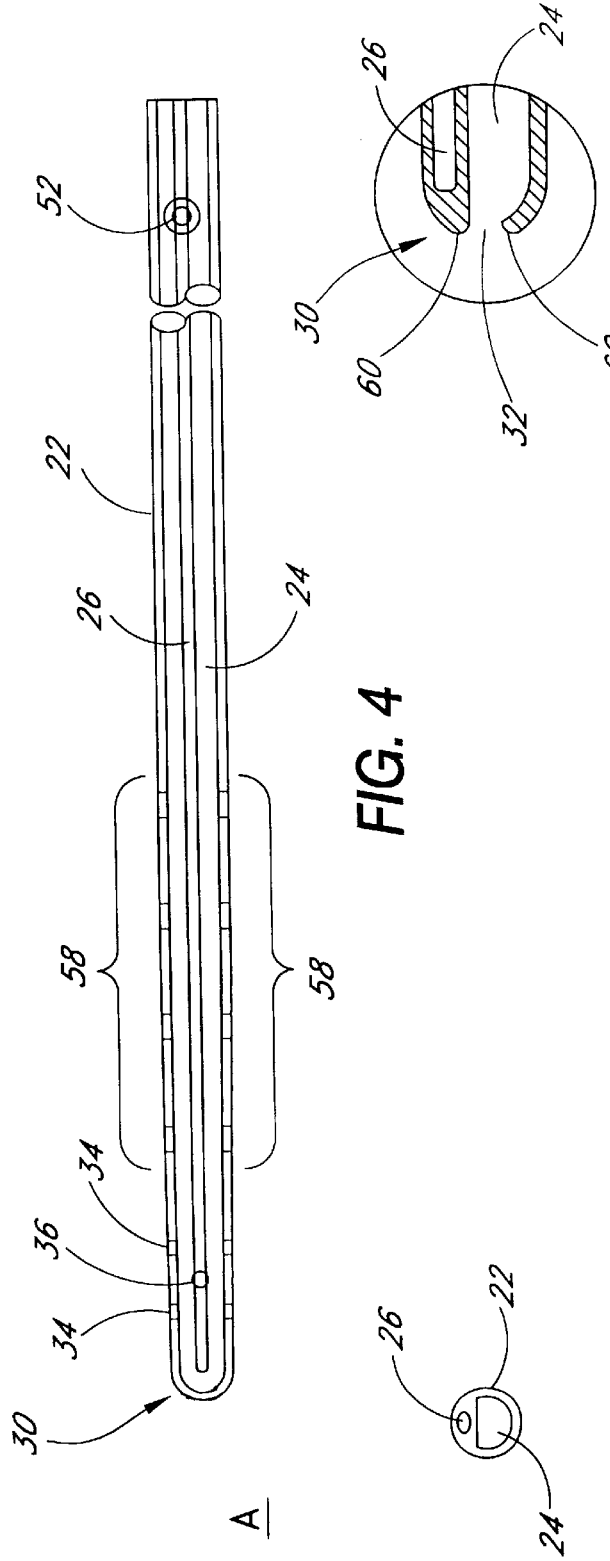

RETROGRADE CARDIOPLEGIA CATHETER

BACKGROUND OF THE INVENTION

1. Field of the Invention

The present invention relates generally to a catheter for use in the clinical arrest of a beating heart, and more specifically to catheter for the retrograde administration of a cardioplegic fluid to the vasculature of the heart.

2. Description of the Related Art

When performing cardiac surgery, it is frequently necessary to temporarily arrest the beating of the patient's heart before the desired surgery can be performed. The procedure for stopping the patient's heart during surgery is known as cardioplegia. One recognized technique of performing cardioplegia is to introduce a cardioplegic fluid, typically a solution containing agents such as potassium, magnesium, or procaine, into the coronary arteries or veins, which supply blood to the heart muscle. This typically occurs after disconnecting the heart from the body's circulatory system, the heart's functions having been assumed by a heart-lung machine. The cardioplegic fluid interferes with the heart muscle's response to electrical signals which normally command it to beat, thereby stopping the heart.

A surgeon can introduce cardioplegic fluid to the coronary-vessel system in either the antegrade direction, which is in the natural direction of blood flow, or in the retrograde direction, which is opposite the natural direction of blood flow. In antegrade cardioplegia, the cardioplegic fluid is directed into the coronary arteries, usually by injecting the fluid into the aorta near the coronary ostia, which join the coronary artery system to the aorta. The fluid then flows into the ostia and the coronary arteries, and eventually to the heart muscle itself.

Retrograde cardioplegia is often performed by infusing a cardioplegic solution into the coronary sinus, which is a sort of collection point into which drains most of the coronary blood supply through the coronary vein system. This infusion is done by inserting a catheter into the coronary sinus and injecting the cardioplegic fluid through the catheter. The catheter typically has a balloon which inflates to seal the opening of the coronary sinus, and one or more openings on the catheter distal of the balloon. The cardioplegic fluid flows the length of the catheter, exits at the distal openings, and then flows into the coronary sinus. From there it flows into the coronary veins to achieve cardioplegia. The balloon prevents the fluid from flowing back out of the coronary sinus in the undesired antegrade direction.

Various types of catheter have been developed for use in retrograde cardioplegia, but all have suffered from one or more drawbacks. Often the catheter incorporates a distal tip which either blunt or cut at an angle. This type of tip may have edges that can damage the tissues of the veins or coronary sinus during insertion of the catheter. Prior art catheters generally feature a cannula which has a uniform width all the way to the distal tip, which can make it difficult for the surgeon to insert the distal end of such a catheter into the veins or sinus. Another problem frequently observed is a catheter with only transverse infusion openings, which are formed in the sidewalls of the cannula, or only an axial infusion opening, at the very tip of the cannula. This type of catheter is easily occluded at the distal end, either by a vessel structure which fits very closely around the cannula sidewalls, or by an obstruction in the vessel just distal of the catheter tip.

SUMMARY OF THE INVENTION

One aspect of the invention is an improved retrograde cardioplegia catheter.

Another aspect of the invention is a retrograde cardioplegia catheter which is easier to insert into the veins or coronary sinus.

Yet another aspect of the invention is a retrograde cardioplegia catheter which will not cause trauma to coronary tissues when being inserted.

Still another aspect of the invention is a retrograde cardioplegia catheter which may incorporate the above features with a self-inflating balloon and a pressure monitoring capability.

Accordingly, there is provided a catheter having an elongated cannula with an infusion lumen, and a portion of the cannula which tapers to form a distal end which is narrower than the more proximal portions of the cannula. The distal end of the cannula forms at least one infusion lumen opening. A balloon is attached to and surrounds the cannula near the distal end while being in fluid communication with the infusion lumen through one or more inflation openings. The infusion lumen openings are smaller than the inflation openings so as to make the balloon self-inflating.

BRIEF DESCRIPTION OF THE DRAWINGS

FIG. 2 is a cross-sectional end view of the cannula of a retrograde cardioplegia catheter;

FIG. 3 is a cross-sectional side view of the distal portion of the cannula;

FIG. 4 is a cross-sectional top view of the distal portion of the cannula;

FIG. 5 is a cross-sectional side view of the distal tip of the cannula;

DETAILED DESCRIPTION OF THE PREFERRED EMBODIMENT

Figure 1:
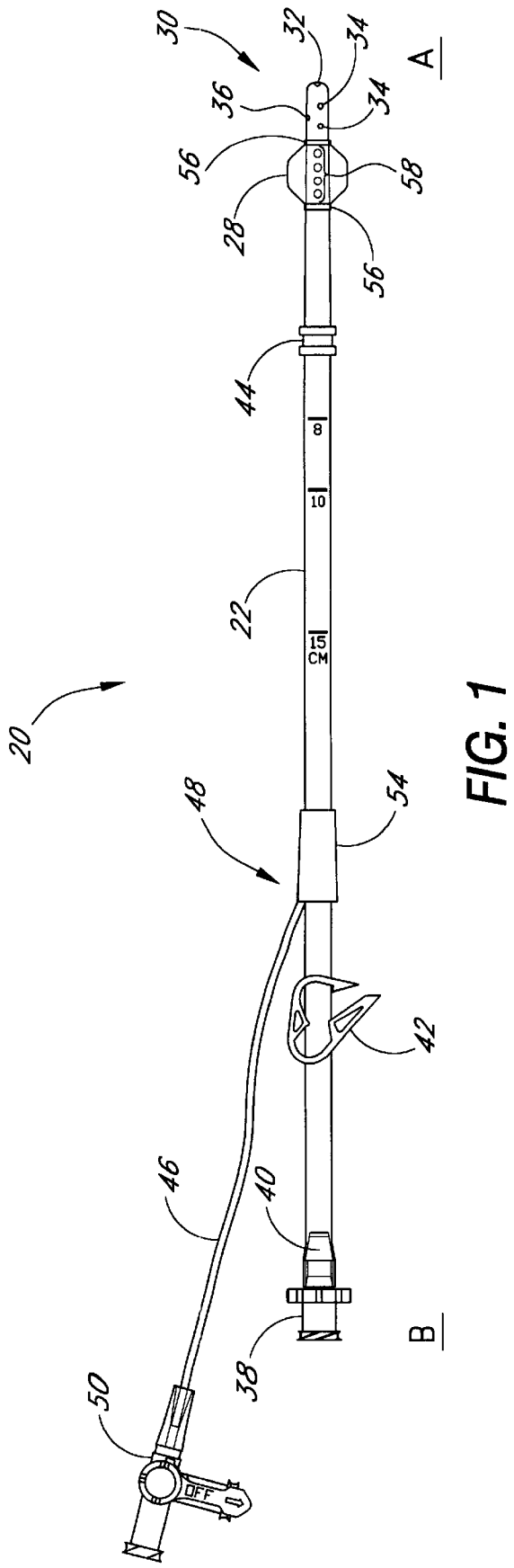
FIG. 1 is a plan view of a retrograde cardioplegia catheter in accordance with the present invention.

FIGS. 1–4 and 6 show one embodiment of a retrograde cardioplegia catheter 20 in accordance with the present invention. As is customary in the art, the terminology used herein will refer to a distal end (marked with the letter A) of the catheter, meaning at or near that end of the catheter 20 which is inserted into a patient's body when in use, and a proximal end (marked with the letter B) of the catheter 20 which generally remains outside of the patient's body during surgery. Furthermore, the preferred dimensions disclosed herein are suitable for use in a commonly-used size 15 French catheter, and will vary proportionately as the size of catheter increases or decreases.

The catheter 20 consists of a flexible cannula 22, preferably constructed of PVC, silicone, or polyurethane, or a coextrusion of two or more layered materials. Preferably, the cannula 22 has two internal lumens: an infusion lumen 24 and a smaller pressure-sensing lumen 26. Alternatively, the pressure-sensing lumen 26 may be omitted where unnecessary. The relation of the two lumens 24, 26 in the cannula 22 is best seen in cross-section in FIG. 2. The infusion lumen 24 and the pressure-sensing lumen 26 run the entire length of the cannula 22, but the pressure-sensing lumen 26 is occluded at both the distal and the proximal ends, as will be further detailed below.

A balloon 28 is located near the distal end A of the cannula 20, but proximal of a rounded distal tip 30. The distal tip 30 forms an axial infusion lumen opening 32 which, in cooperation with transverse infusion lumen openings 34, provides a distal outlet for cardioplegic fluid introduced into the proximal end of the infusion lumen 24. A pressure-sensing lumen inlet 36, which provides an entryway for ambient fluid into the distal end of the pressure-sensing lumen 26, is adjacent the infusion lumen outlets 32, 34.

The proximal end B of the cannula 22 includes a locking luer 38 with a connection fitting 40 tightly received within the infusion lumen 24. The luer 38 provides a connection for a cardioplegic fluid source (not shown) to introduce a cardioplegic fluid into the infusion lumen 24. The luer 38 also occludes and seals the pressure-sensing lumen 26 at the proximal end, to prevent cardioplegic fluid from entering the pressure-sensing lumen 26. A clamp 42, shown in FIGS. 1 and 6 in the open position, permits selective closure of the infusion lumen 24. A suture guide 44 is moveable along the cannula 22 and facilitates anchoring of the catheter 20 during surgery via appropriate suturing as is known in the art.

To permit connection to a pressure monitoring device (not shown), a tube in the form of a pressure-sensing branch 46 extends from a junction 48 to a three-way stopcock 50. At the junction 48, the distal end of the pressure-sensing branch 46 sealingly engages the pressure-sensing lumen 26 by entering a pressure-sensing notch 52 (best seen in FIGS. 3 and 4). The pressure-sensing notch 52 is preferably bowl-shaped, with a preferred diameter decreasing from about 0.100" at the outer surface of the cannula 22, to about 0.051" at the greatest depth of the pressure-sensing notch 52. The vertical axis of the notch is located about 8" proximal of the distal end A of the cannula 22. A sleeve 54 covers the junction 48 tightly, but permits fluid communication between the pressure-sensing inlet 36, pressure-sensing lumen 26, pressure-sensing branch 46, and three-way stopcock 50.

In the preferred embodiment, the distal portion of the cannula 22 tapers inward, from a point on the cannula 22 near the balloon 28, to the distal end A. Preferably, in the commonly used 15 French size, the cannula 22 tapers inward along about 1.2" of the most distal portion of the cannula 22, from a 15 French size (corresponding to an outside diameter of about 0.196") to a 13 French size (outside diameter of about 0.169") at the far distal point of the cannula, immediately proximal of the rounded distal tip 30. With the tapering, the cross-sectional area of the infusion lumen 24 varies within a preferred range of about 0.0109 to about 0.0081 square inches, and the cross-sectional area of the pressure-sensing lumen 26 varies within a preferred range of about 0.0049 to about 0.0066 square inches.

Figure 6:
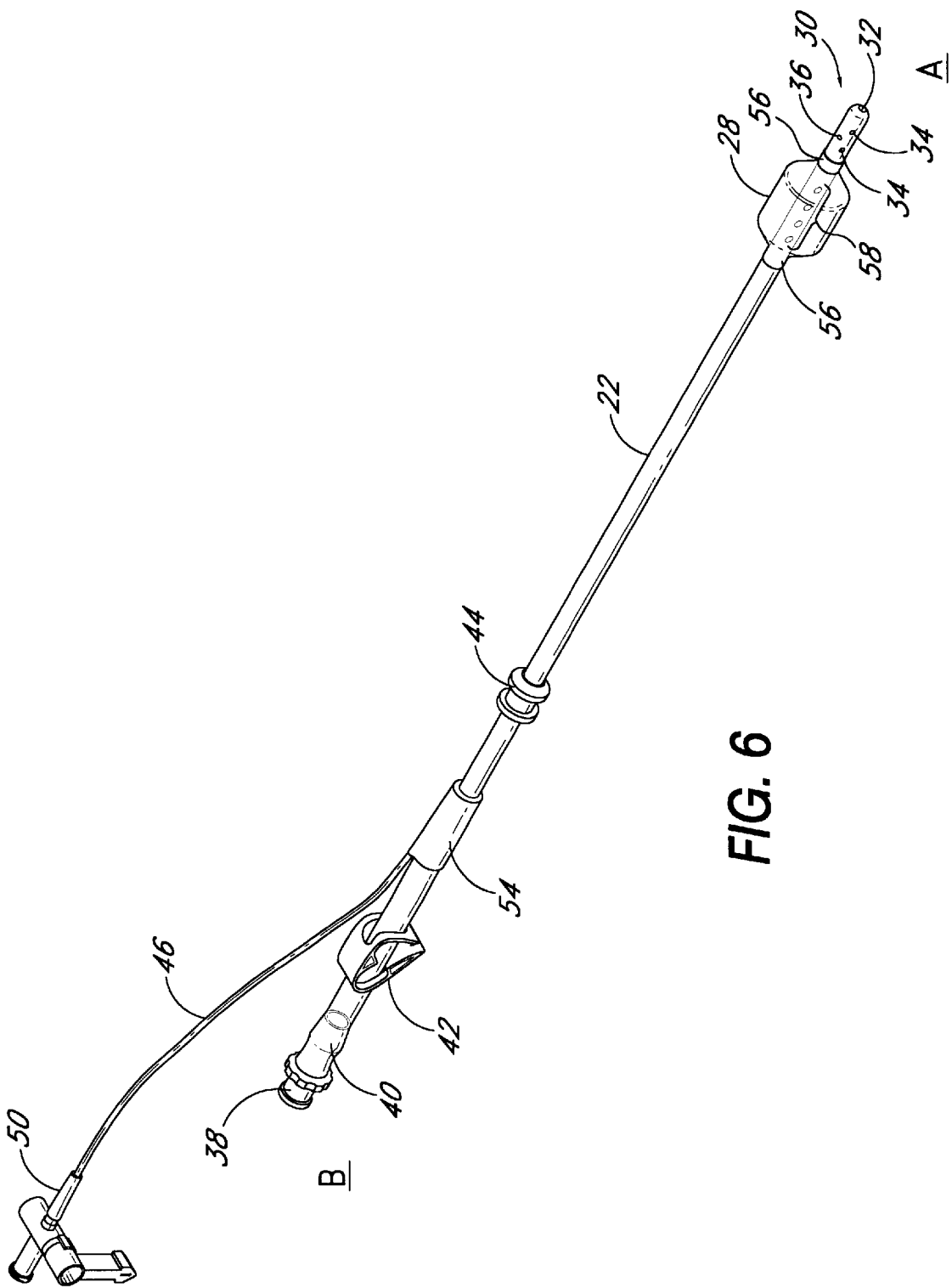
FIG. 6 is a perspective view of a retrograde cardioplegia catheter in accordance with the present invention.

FIGS. 1 and 6 best depict the attachment of the balloon 28 to the cannula 22. The balloon 28 is sealingly attached to the circumference of the cannula 22 at attachment points 56, preferably by solvent bonding, UV bonding, or other techniques known in the art. Preferably, the balloon 28 is about 0.55" to 0.79" in diameter and is positioned on the cannula 22 such that its distal end (not inclusive of the attachment points 56) is about 0.50" proximal of the distal end A of the cannula 22. Between the attachment points 56, the balloon 28 completely surrounds and is generally coaxial with the cannula 22.

Preferably constructed of dip-molded or blow-molded PVC, or polyurethane, the balloon 28 is fluid-tight and forms a chamber around the cannula 22. Advantageously, the surface of the balloon 28 has a texture which is uneven but lacks any burrs or sharp protrusions. This uneven texture improves the balloon's ability to hold its position in the coronary sinus by frictionally engaging the walls of the sinus. Such a balloon can be made by sand-blasting the surface of the mold to add the desired texture, and then employing the customary molding process. The resulting balloon has the desired uneven surface but without the burrs which may damage the coronary sinus.

The balloon 28 is preferably of the self-inflating type, but alternatively the balloon 28 may be inflatable via an additional dedicated inflation lumen (not shown). The preferred balloon 28 is in fluid communication with the infusion lumen 24 through inflation openings 58 formed in the walls of the cannula 22. Thus, cardioplegic solution introduced into the infusion lumen 24 can flow through the inflation openings 58 into the balloon 28, and from the balloon 28 back into the infusion lumen 24. Advantageously, the total cross-sectional area of the inflation openings 58 exceeds the total area of the infusion lumen openings 32, 34, and exceeds that of the narrowest portion of the infusion lumen 24. As seen in FIGS. 3 and 4, there are preferably a total of eight inflation openings 58, four on each of two opposite sides of the cannula 22. In a 15 French catheter, the preferred size for each of the eight inflation openings 58 is a diameter of about 0.070".

FIGS. 3 and 4 best depict the preferred location and relative sizes of the axial infusion lumen opening 32 and the transverse infusion lumen openings 34. Advantageously, the total cross-sectional area of the infusion lumen openings 32, 34 is less than that of the narrowest portion of the infusion lumen 24. The preferred embodiment has four transverse infusion lumen openings 34, two on each of two opposite sides of the cannula 22, and a single axial infusion lumen opening in the distal tip 30. In a 15 French catheter, the preferred size for each of the four transverse infusion lumen openings 34 is a diameter of about 0.040", and the axial infusion lumen opening 32 is preferably about 0.0425" in diameter. The distal pair of transverse infusion lumen openings are centered about an axis which is preferably about 0.25" proximal of the distal end A of the cannula 22.

The tapered cannula 22, and the relative sizes of the infusion lumen 24 and infusion lumen openings 32, 34, coact to create a back pressure in the infusion lumen 24 upon introduction of a cardioplegic fluid flowing from the proximal end to the distal end of the lumen. Both the tapering and the relatively smaller openings restrict the flow of the fluid as it reaches the distal end of the infusion lumen 24, increasing the fluid pressure along the lumen. The relatively large inflation openings 58 in the infusion lumen 24 allow the fluid to flow into the balloon 28 with little resistance, relieving the back pressure until the balloon 28 is full. At this point the back pressure is exerted against the walls of the balloon 28, maintaining the balloon 28 in an inflated, distended shape. Thus the arrangement of the tapered cannula 22 with relatively small infusion lumen openings 32, 34 and relatively large inflation openings 58, imparts a self-inflating effect to the balloon 28, and eliminates the need for a separate balloon inflation lumen.

The tapered cannula 22 provides other advantages in the use of the catheter 20. One such advantage is that for a given catheter size the tapered distal portion of the cannula 22 facilitates easier insertion of the catheter 20 into a patient's vasculature, including the coronary sinus. This reduces the difficulty of inserting the catheter and reduces the chance of causing trauma to the associated tissues during insertion.

FIG. 5 shows the distal tip 30 of the cannula 22 in greater detail. The distal tip 30 is rounded, preferably by molding the distal end of the cannula 22, and incorporates the axial infusion lumen opening 32 while occluding the pressure-sensing lumen 26. Preferably, the distal tip 30 is further rounded at the edges of the axial infusion lumen opening 32. When used with a 15 French catheter, the distal tip 30 is rounded on each side with a preferred radius of about 0.085", and at the edges of the axial infusion lumen opening 32 with a preferred radius of about 0.016". By rounding the distal tip 30 one avoids sharp edges which may cause injury to the tissues of the coronary sinus and surrounding areas during insertion of the catheter 20.

FIGS. 1, 3, 4, and 6 show the location of the pressure-sensing inlet 36 relative to the other structures near the distal end of the cannula 22. The pressure-sensing inlet 36, and the associated pressure-sensing lumen 26 and pressure-sensing branch 46, permit a surgeon to monitor the fluid pressure in the coronary sinus during infusion of cardioplegic solution, so as to avoid excessive pressures which could result in injury to the surrounding tissues. Having a preferred diameter of about 0.045", the pressure-sensing inlet 36 is advantageously located about 90° away from the transverse infusion lumen openings 34 on the wall of the cannula 22, and is centered about an axis which is approximately 0.340" proximal of the distal tip 30. This position is chosen to prevent the flow of cardioplegic solution exiting the infusion lumen openings 32, 34 from affecting the pressure readings at the pressure-sensing inlet 36.

Figure 7:
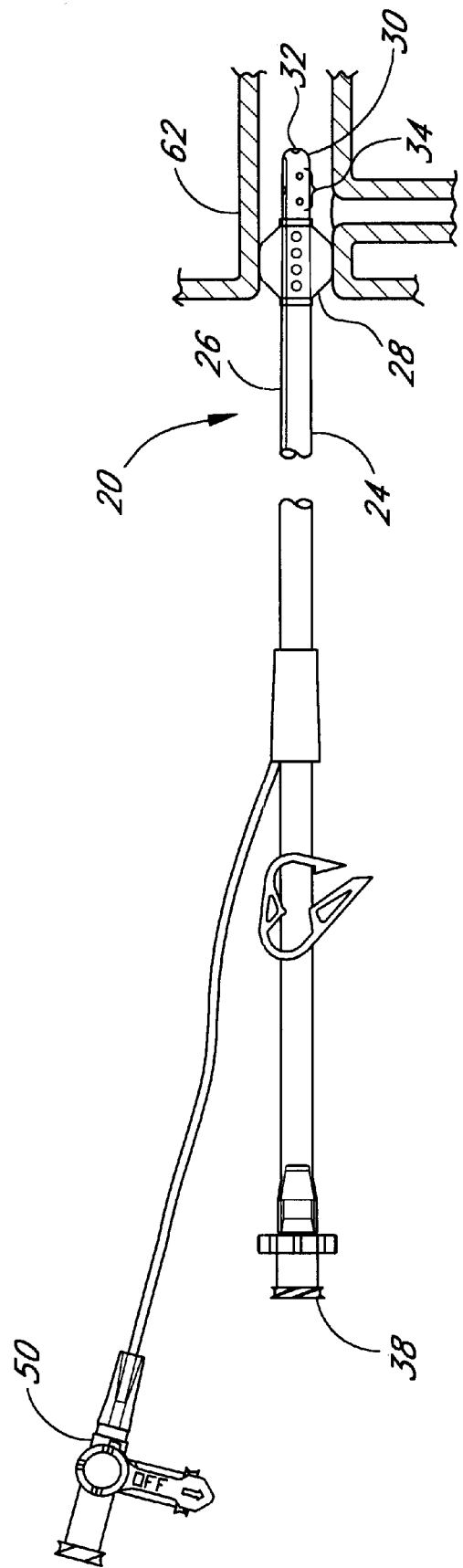
FIG. 7 is a schematic view of the distal end of retrograde cardioplegia catheter inserted into the coronary sinus.

FIG. 7 shows the positioning of the catheter 20 during its use in performing retrograde cardioplegia. The distal end of the catheter 20 is inserted into the coronary sinus 62 in a manner known to those skilled in the art. A wire stylet (not shown) may be inserted into the cannula 22 to provide assistance in inserting and manipulating the catheter 20, and removed when the catheter 20 is in place. The balloon 28 is positioned to occupy the opening of the sinus 62, with the distal tip 30 within the sinus 62 and pointing generally in the retrograde direction. After venting any air from the infusion and sensing lumens 24, 26, a cardioplegic fluid source (not shown) is connected to the luer 38, and a pressure monitoring device (not shown) is connected to the stopcock 50.

Using the cardioplegic fluid source, the surgeon introduces a cardioplegic fluid, containing agents such as potassium, magnesium, procaine, or a hypocalcemic solution, into the infusion lumen 24 of the catheter 20. The fluid fills the balloon 28 to a pressure exceeding that in the coronary sinus 62 and exits to the sinus via infusion lumen openings 32, 34. The pressurized balloon 28 conforms to the walls of the coronary sinus 62, creating a seal which prevents the cardioplegic fluid from flowing in the antegrade direction. Instead, the catheter 20 infuses the fluid in the retrograde direction, into the coronary vasculature, achieving cardioplegia. The balloon 28 and catheter 20 may remain in place during the operation to provide periodic re-infusions of cardioplegic fluid as necessary.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A retrograde cardioplegia catheter, comprising:
    an elongated, flexible cannula with a distal end and a proximal end, and an infusion lumen, the cannula tapering outward from the distal end to a point at least part of the way toward the proximal end;
    a balloon attached to and surrounding the cannula near the distal end, the balloon being in fluid communication with the infusion lumen through at least one inflation opening; and
    at least one infusion lumen opening on the cannula distal of the balloon;
    wherein the sum of the total cross-sectional area of the at least one inflation opening is larger than the sum of the total cross-sectional area of the at least one infusion lumen opening, so as to impart a self-inflating effect to the balloon when a cardioplegic solution is introduced into the infusion lumen.

2. The catheter of claim 1 further comprising a rounded distal tip on the cannula.

3. The catheter of claim 1 wherein the balloon has a textured surface.

4. The catheter of claim 1 wherein said balloon is formed from PVC.

5. The catheter of claim 1 wherein the at least one infusion lumen opening comprises at least one axial infusion lumen opening in a distal tip of the cannula and at least one transverse infusion lumen opening in the cannula wall proximal of the at least one axial infusion lumen opening.

6. The catheter of claim 1 wherein the balloon has a surface with an uneven texture.

7. A retrograde cardioplegia catheter, comprising:
    an elongated, flexible cannula with a distal end and a proximal end, and an infusion lumen, the cannula tapering outward from the distal end to a point at least part of the way toward the proximal end;
    a balloon attached to and surrounding the cannula near the distal end, the balloon being in fluid communication with the infusion lumen through at least one inflation opening; and
    at least one infusion lumen opening on the caxmula distal of the balloon;
    wherein the sun of the total cross-sectional area of the at least one inflation opening is larger than the sum of the total cross-sectional area of the at least one infusion lumen opening, so as to impart a self-inflating effect to the balloon when a cardioplegic solution is introduced into the infusion lumen;
    further comprising a pressure-sensing lumen in the cannula and a pressure-sensing inlet on the cannula distal of the balloon and in fluid communication with the pressure-sensing lumnen.

8. A retrograde cardioplegia catheter, comprising:
    an elongated, flexible cannula with a distal end and a proximal end and an infusion lumen, the cannula tapering outward from the distal end to a point at least part of the way toward the proximal end;
    a balloon attached to and surrounding the cannula near the distal end, the balloon being in fluid communication with the infusion lumen through at least one inflation opening; and
    at least one infusion lumen opening on the cannula distal of the balloon;
    wherein the sum of the total cross-sectional area of the at least one inflation opening is larger than the sum of the total cross-sectional area of the at least one infusion lumen opening, so as to inpart a self-inflating effect to the balloon when a cardioplegic solution is introduced into the infusion lumnen;

further comprising a rounded distal tip on the cannula;

wherein the at least one infusion lumen opening comprises at least one axial infusion lumen opening in the distal tip and at least one transverse infusion lumen opening in the cannula wall proximal of the at least one axial infusion lumen opening.

9. A retrograde cardioplegia catheter, comprising:

an elongated, flexible cannula with a distal end and a proximal end, and an infusion lumen, the cannula tapering outward from the distal end to a point at least part of the way toward the proximal end;

a balloon attached to and surrounding the cannula near the distal end, the balloon being in fluid communication with the infusion lumen through at least one inflation opening; and at least one infusion lumen opening on the cannula distal of the balloon;

wherein the sum of the total cross-sectional area of the at least one inflation opening is larger than the sum of the total cross-sectional area of the at least one infusion lumen opening, so as to impart a self-inflating effect to the balloon when a cardioplegic solution is introduced into the infusion lumen;

wherein the cannula tapers to its distal end from about a 15 French size to about a 13 French size along approximately 1.2 inches of the cannula.

10. A retrograde cardioplegia catheter, comprising:

an elongated, flexible cannula with a distal end and a proximal end, and an infusion lumen, the cannula tapering outward from the distal end to a point at least part of the way toward the proximal end;

a balloon attached to and surrounding the cannula near the distal end, the balloon being in fluid communication with the infusion lumen through at least one inflation opening; and at least one infusion lumen opening on the cannula distal of the balloon;

wherein the sum of the total cross-sectional area of the at least one inflation opening is larger than the sum of the total cross-sectional area of the at least one infusion lumen opening, so as to impart a self-inflating effect to the balloon when a cardioplegic solution is introduced into the infusion lumen, wherein the cannula tapers from an infusion lumen cross-sectional area of about 0.0109 square inches to about 0.0081 square inches.

11. A catheter, comprising:

an elongated, flexible cannula with a distal end and a proximal end, and an infusion lumen, the cannula tapering outward from the distal end to a point at least part of the way toward the proximal end;

a balloon attached to the cannula near the distal end, said balloon configured to self-inflate upon introduction of a fluid into said infusion lumen; and at least one infusion lumen opening on the cannula distal of the balloon.

12. The catheter of claim 11 further comprising a pressure-sensing lumen in the cannula and a pressure-sensing inlet on the cannula distal of the balloon and in fluid communication with the pressure sensing lumen.

13. The catheter of claim 11 further comprising a rounded distal tip on the cannula.

14. The catheter of claim 11 wherein the at least one infusion lumen opening comprises at least one axial infusion lumen opening in a distal tip of the cannula and at least one transverse infusion lumen opening in the cannula wall proximal of the at least one axial infusion lumen opening.

15. The catheter of claim 11 wherein the cannula tapers to its distal end from about a 15 French size to about a 13 French size along approximately 1.2 inches of the cannula.

16. The catheter of claim 11 wherein the cannula tapers from an infusion lumen cross-sectional area of about 0.0109 square inches to about 0.0081 square inches.

17. The catheter of claim 11 wherein the balloon has a textured surface.

18. The catheter of claim 11 wherein the balloon has a surface with an uneven texture.

19. The catheter of claim 11 wherein said balloon is formed from PVC.

20. A method for inducing cardioplegia, comprising the steps of:

providing a catheter having:

an elongated, flexible cannula with a distal end and a proximal end, and an infusion lumen, the cannula tapering outward from the distal end to a point at least part of the way toward the proximal end;

a balloon attached to and surrounding the cannula near the distal end, the balloon being in fluid communication with the infusion lumen through at least one inflation opening; and at least one infusion lumen opening on the cannula distal of the balloon, the total cross-sectional area of the at least one inflation opening being larger than the total cross-sectional area of the at least one infusion lumen opening;

inserting the catheter at least partway into the coronary sinus so that the balloon is positioned in the opening of the coronary sinus and the distal tip is disposed within the coronary sinus; and injecting a cardioplegic solution into the infusion lumen so that it flows to the distal end, fills the balloon to seal the opening of the coronary sinus, and flows out the infusion lumen opening.

21. The method of claim 20, further comprising monitoring the fluid pressure in the coronary sinus.

22. The method of claim 20, wherein said catheter further comprises a pressure-sensing lumen in the cannula and a pressure-sensing inlet on the cannula distal of the balloon and in fluid communication with the pressure-sensing lumen.

23. The method of claim 20, wherein the at least one infusion lumen opening comprises at least one axial infusion lumen opening in a distal tip of the cannula and at least one transverse infusion lumen opening in the cannula wall proximal of the at least one axial infusion lumen opening.

24. The method of claim 20, wherein the cannula tapers to its distal end from about a 15 French size to about a 13 French size along approximately 1.2 inches of the cannula.

25. The method of claim 20 wherein the cannula tapers from an infusion lumen cross-sectional area of about 0.0109 square inches to about 0.0081 square inches.

26. The method of claim 20 wherein tie balloon has a textured surface.

27. The method of claim 20 wherein the balloon has a surface with an uneven texture.

28. The method of claim 20 wherein said balloon is formed from PVC.

* * * * *

UNITED STATES PATENT AND TRADEMARK OFFICE
CERTIFICATE OF CORRECTION

PATENT NO.    : 6,500,145 B1
DATED         : December 31, 2002
INVENTOR(S)   : Mehmet Bicakci and Sheryl W. Higgins It is certified that error appears in the above-identified patent and that said Letters Patent is hereby corrected as shown below:

<u>Column 8,</u>
Line 60, please replace "tie" with -- the --

Signed and Sealed this

Nineteenth Day of August, 2003

JAMES E. ROGAN
*Director of the United States Patent and Trademark Office*